(12) United States Patent
Khosravi et al.

(10) Patent No.: US 8,382,797 B2
(45) Date of Patent: Feb. 26, 2013

(54) METHODS FOR SEALING A VASCULAR PUNCTURE

(75) Inventors: Farhad Khosravi, Los Altos Hills, CA (US); Suresh S. Pai, Mountain View, CA (US); Celso J. Bagaoisan, Union City, CA (US); Scott R. Sershen, Belmont, CA (US); Marlon Moreno, San Jose, CA (US); Juan Domingo, Union City, CA (US)

(73) Assignee: AccessClosure, Inc., Mountain View, CA (US)

( * ) Notice: Subject to any disclaimer, the term of this patent is extended or adjusted under 35 U.S.C. 154(b) by 0 days.

(21) Appl. No.: 13/587,781

(22) Filed: Aug. 16, 2012

(65) Prior Publication Data

US 2012/0310276 A1 Dec. 6, 2012

Related U.S. Application Data

(63) Continuation of application No. 11/854,534, filed on Sep. 12, 2007.

(60) Provisional application No. 60/825,410, filed on Sep. 13, 2006.

(51) Int. Cl.
*A61B 17/08* (2006.01)

(52) U.S. Cl. .................. 606/213; 606/214; 606/215

(58) Field of Classification Search .......... 606/213–215; 604/15, 288
See application file for complete search history.

(56) References Cited

U.S. PATENT DOCUMENTS

| | | | |
|---|---|---|---|
| 2,365,039 A | 12/1944 | Andresen | |
| 3,765,419 A | 10/1973 | Usher | |
| 4,002,173 A | 1/1977 | Manning | |
| 4,472,542 A | 9/1984 | Nambu | |
| 4,655,211 A | 4/1987 | Sakamoto | |
| 4,664,857 A | 5/1987 | Nambu | |
| 4,734,097 A | 3/1988 | Tanabe | |
| 4,738,658 A | 4/1988 | Magro | |
| 4,790,819 A | 12/1988 | Li et al. | |
| 4,838,280 A | 6/1989 | Haaga | |
| 4,852,568 A | 8/1989 | Kensey | |
| 4,890,612 A | 1/1990 | Kensey | |
| 5,021,059 A | 6/1991 | Kensey et al. | |
| 5,061,274 A | 10/1991 | Kensey | |
| 5,108,421 A | 4/1992 | Fowler | |
| 5,192,302 A | 3/1993 | Kensey | |
| 5,221,259 A | 6/1993 | Weldom | |

(Continued)

FOREIGN PATENT DOCUMENTS

| | | |
|---|---|---|
| EP | 476178 | 3/1992 |
| WO | WO 9222252 | 12/1992 |

(Continued)

OTHER PUBLICATIONS

PCT International Search Report and Written Opinion for PCT/US2007/078328; Applicant: Accessclosure, Inc. et al; Forms PCT/ISA/210, PCT/ISA/237, and PCT/ISA/220; Dated Oct. 2005, 20 pages.

(Continued)

*Primary Examiner* — Gregory Anderson
(74) *Attorney, Agent, or Firm* — Knobbe Martens Olson & Bear LLP

(57) ABSTRACT

A method for sealing a puncture through a vessel wall using a sealing device including an elongate tubular body, a balloon carried by the body, an outer tubular member carried over the elongate tubular body, and a sealant carried by the elongate tubular body adjacent the balloon. Retracting the outer tubular member exposes the sealant.

5 Claims, 7 Drawing Sheets

U.S. PATENT DOCUMENTS

| | | | |
|---|---|---|---|
| 5,228,851 A | 7/1993 | Burton | |
| 5,258,042 A | 11/1993 | Mehta | |
| 5,275,616 A | 1/1994 | Fowler | |
| 5,290,310 A | 3/1994 | Makower | |
| 5,292,332 A | 3/1994 | Lee | |
| 5,310,407 A | 5/1994 | Casale | |
| 5,320,639 A * | 6/1994 | Rudnick | 606/213 |
| 5,324,306 A | 6/1994 | Makower | |
| 5,334,216 A | 8/1994 | Vidal | |
| 5,370,660 A | 12/1994 | Weinstein | |
| 5,383,896 A | 1/1995 | Gershony | |
| 5,391,183 A | 2/1995 | Janzen et al. | |
| 5,409,703 A | 4/1995 | McAnalley | |
| 5,413,571 A | 5/1995 | Katsaros | |
| 5,419,765 A | 5/1995 | Weldon | |
| 5,431,639 A | 7/1995 | Shaw | |
| 5,437,292 A | 8/1995 | Kipshidze | |
| 5,437,631 A | 8/1995 | Janzen | |
| 5,441,517 A | 8/1995 | Kensey | |
| 5,464,396 A | 11/1995 | Barta | |
| 5,486,195 A | 1/1996 | Myers | |
| 5,514,158 A | 5/1996 | Kanesaka | |
| 5,529,577 A | 6/1996 | Hammerslag | |
| 5,550,187 A | 8/1996 | Rhee | |
| 5,571,181 A | 11/1996 | Li | |
| 5,580,923 A | 12/1996 | Yeung | |
| 5,591,205 A | 1/1997 | Fowler | |
| 5,601,602 A | 2/1997 | Fowler | |
| 5,626,601 A | 5/1997 | Gershony | |
| 5,643,464 A | 7/1997 | Rhee | |
| 5,700,477 A | 12/1997 | Rosenthal | |
| 5,716,375 A | 2/1998 | Fowler | |
| 5,718,916 A | 2/1998 | Scherr | |
| 5,725,498 A | 3/1998 | Janzen | |
| 5,725,551 A | 3/1998 | Myers | |
| 5,744,153 A | 4/1998 | Yewey | |
| 5,752,974 A | 5/1998 | Rhee | |
| 5,780,044 A | 7/1998 | Yewey | |
| 5,782,860 A | 7/1998 | Epstein | |
| 5,836,970 A | 11/1998 | Pandit | |
| 5,868,778 A | 2/1999 | Gershony | |
| 5,916,236 A | 6/1999 | Muijs Van de Moer | |
| 5,928,266 A | 7/1999 | Kontos | |
| 5,948,429 A | 9/1999 | Bell | |
| 5,948,829 A | 9/1999 | Wallajapet | |
| 5,951,583 A | 9/1999 | Jensen | |
| 5,957,952 A | 9/1999 | Gershony | |
| 5,972,375 A | 10/1999 | Truter | |
| 5,973,014 A | 10/1999 | Funk | |
| 6,017,359 A | 1/2000 | Gershony | |
| 6,022,361 A | 2/2000 | Epstein | |
| 6,048,358 A | 4/2000 | Barak | |
| 6,051,248 A | 4/2000 | Sawhney | |
| 6,056,768 A | 5/2000 | Cates et al. | |
| 6,056,769 A | 5/2000 | Epstein | |
| 6,063,061 A | 5/2000 | Wallace | |
| 6,083,522 A | 7/2000 | Chu | |
| 6,152,943 A | 11/2000 | Sawhney | |
| 6,162,240 A | 12/2000 | Cates | |
| 6,162,241 A | 12/2000 | Coury | |
| 6,165,201 A | 12/2000 | Sawhney | |
| 6,179,862 B1 | 1/2001 | Sawhney | |
| 6,238,412 B1 | 5/2001 | Dubrul | |
| 6,271,278 B1 | 8/2001 | Park | |
| 6,287,323 B1 | 9/2001 | Hammerslag | |
| 6,302,898 B1 | 10/2001 | Edwards | |
| 6,325,789 B1 | 12/2001 | Janzen | |
| 6,350,274 B1 | 2/2002 | Li | |
| 6,371,975 B2 | 4/2002 | Cruise | |
| 6,458,147 B1 | 10/2002 | Cruise | |
| 6,475,177 B1 | 11/2002 | Suzuki | |
| 6,514,534 B1 | 2/2003 | Sawhney | |
| 6,562,059 B2 | 5/2003 | Edwards | |
| 6,566,406 B1 | 5/2003 | Pathak | |
| 6,569,185 B2 | 5/2003 | Ungs | |
| 6,605,294 B2 | 8/2003 | Sawhney | |
| 6,608,117 B1 | 8/2003 | Gvozdic | |
| 6,610,026 B2 | 8/2003 | Cragg | |
| 6,613,070 B2 | 9/2003 | Redmond | |
| 6,626,861 B1 | 9/2003 | Hart | |
| 6,635,068 B1 | 10/2003 | Dubrul | |
| 6,689,148 B2 | 2/2004 | Sawhney | |
| 6,699,261 B1 | 3/2004 | Cates et al. | |
| 6,703,047 B2 | 3/2004 | Sawhney | |
| 6,774,151 B2 | 8/2004 | Malmgren | |
| 6,818,008 B1 | 11/2004 | Cates | |
| 6,818,018 B1 | 11/2004 | Sawhney | |
| 6,863,924 B2 | 3/2005 | Ranganathan | |
| 6,887,974 B2 | 5/2005 | Pathak | |
| 6,960,617 B2 | 11/2005 | Omididan | |
| 7,335,220 B2 | 2/2008 | Khosravi | |
| 7,611,479 B2 | 11/2009 | Cragg et al. | |
| 7,621,936 B2 | 11/2009 | Cragg et al. | |
| 7,850,710 B2 | 12/2010 | Huss | |
| 7,955,353 B1 | 6/2011 | Ashby et al. | |
| 2001/0031948 A1 | 10/2001 | Cruise | |
| 2001/0046518 A1 | 11/2001 | Sawhney | |
| 2001/0047187 A1 | 11/2001 | Milo | |
| 2001/0051813 A1 | 12/2001 | Hnojewyj | |
| 2002/0062104 A1 | 5/2002 | Ashby | |
| 2002/0072767 A1 | 6/2002 | Zhu | |
| 2002/0106409 A1 | 8/2002 | Sawhney | |
| 2002/0188319 A1 | 12/2002 | Morris | |
| 2004/0267193 A1 | 12/2004 | Baraoisan | |
| 2004/0267307 A1 | 12/2004 | Bagaoisan | |
| 2004/0267308 A1 * | 12/2004 | Bagaoisan et al. | 606/213 |
| 2006/0034930 A1 | 2/2006 | Khosravi | |
| 2008/0161849 A1 | 7/2008 | Cates et al. | |
| 2010/0211000 A1 | 8/2010 | Killion et al. | |

FOREIGN PATENT DOCUMENTS

| | | |
|---|---|---|
| WO | WO 0014155 | 3/2000 |
| WO | WO 0019912 | 4/2001 |
| WO | WO 03094749 | 11/2003 |

OTHER PUBLICATIONS

Chisholm, et al., *Fibrin Sealant as a Plug for the Post Liver Biopsy Needle Track*, 40(6) Clinical Radiology 627-28 (Nov. 1989).

Clayman, et al. *Renal Vascular Complications Associated with the Percutaneous Removal of Renal Calculi*, 132, The Journal of Urology, 228-230 (Aug. 1984).

Feliciano, *Abstract: Use of Balloon Catheter Tamponade in Vascular Wounds*, 24(7) The Journal of Trauma 657 (Jul. 1984).

Feliciano, et al., *Balloon Catheter Tamponade in Cardiovascular Wounds*, 160 The American Journal of Surgery 583-87 (Dec. 1990).

Gazelle, et al., *Hemostatic Protein-Polymer Sheath: New Method to Enhance Hemostasis at Percutaneous Biopsy*, 175 Radiology 671-74 (Jun. 1990).

Gross, *A Manual of Military Surgery*, Chapter V: Wounds and other injuries, 53-55 (1861).

Kaye, et al. *Tamponade Nephrostomy Catheter for Percutaneous Nephrostolithotomy*, 27(5) Urology 441-45 (May 1986).

Pfab, et al., *Animal Experiments on Hemostasis with a Collagen-Fibrin Tissue-Adhesive Sealant in the Nephrostomy Tract*, 42 Urology International 207-09 (1987).

Pfab et al., *Local Hemostasis of Nephrostomy Tract with Fibrin Adhesive Sealing in Percutaneous Nephrolithotomy*, 13 European Urology 118-21 (1987).

Riley, et al., *Percutaneous Liver Biopsy with Plugging of Needle Track: A Safe Method for Use in Patients with Impaired Coagulation*, The Lancet 436 (Aug. 1984).

Smiley, et al. *Balloon Catheter Tamponade of Major Vascular Wounds*, 121 The American Journal of Surgery 326-27 (Mar. 1971).

Takayasu, et al., *A New Hemostatic Procedure for Percutaneous Transhepatic Portal Vein Catheterization*, 18(3) Japanese Journal of Clinical Oncology 227-30 (Sep. 1988).

* cited by examiner

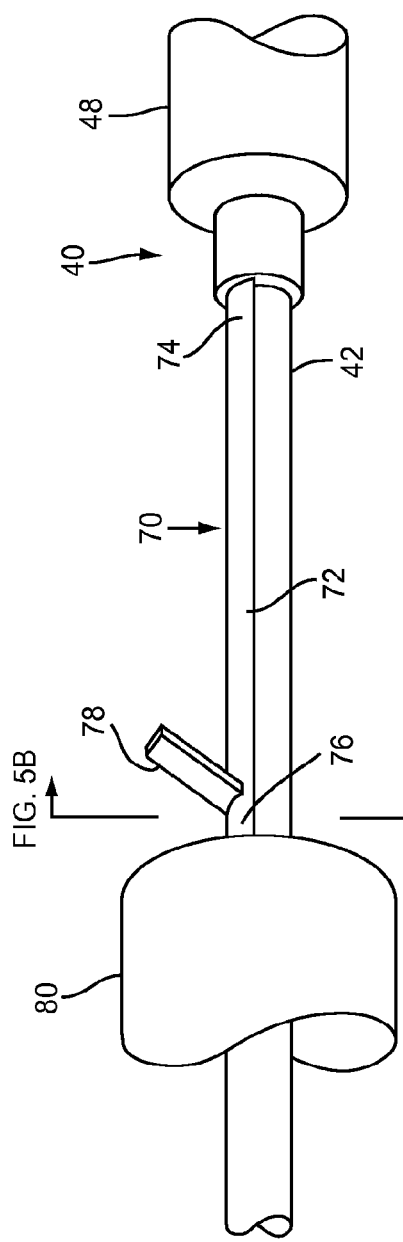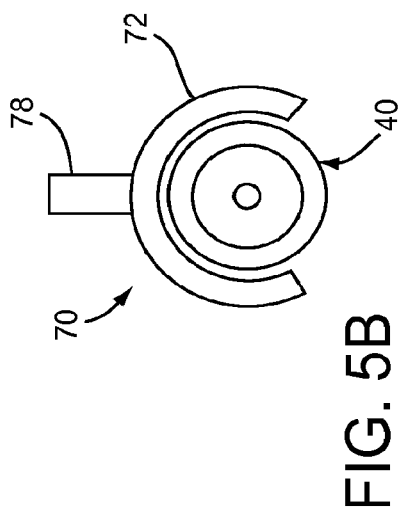
FIG. 5A
FIG. 5B

METHODS FOR SEALING A VASCULAR PUNCTURE

CROSS-REFERENCE TO RELATED APPLICATIONS

This application is a continuation of U.S. patent application Ser. No. 11/854,534, which was filed on Sep. 12, 2007, which claims priority benefit of U.S. Provisional Application Ser. No. 60/825,410, filed Sep. 13, 2006, all of which applications are hereby incorporated by reference in their entirety.

BACKGROUND OF THE INVENTION

1. Field of the Invention

The present invention relates generally to apparatus and methods for sealing punctures in a body, and more particularly, to apparatus and methods for sealing a vascular puncture extending through tissue, and/or to apparatus and methods for delivering a sealant into a percutaneous puncture extending from a patient's skin to a blood vessel or other body lumen to seal the puncture.

2. Description of the Related Art

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate accessing and/or introducing various devices into the vessel, while minimizing trauma to the vessel wall and/or minimizing blood loss. Upon completing the procedure, the device(s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

Accordingly, apparatus and methods for sealing a puncture through tissue would be useful.

SUMMARY OF THE INVENTION

This application is directed toward a method of sealing a puncture through a vessel wall using a sealing device including an elongate tubular body, a balloon carried by the body, an outer tubular member carried over the elongate tubular body, and a sealant carried by the elongate tubular body adjacent the balloon. The method includes providing the sealing device, inflating the balloon inside of the vessel, retracting the outer tubular member to expose the sealant, deflating the balloon, and retracting the balloon through the sealant.

The method may also include tamping the sealant. The tamping step may be accomplished using an elongate tamping tube, slidably carried inside of the outer tubular member. The tubular body may also be proximally retracted through the tamping tube.

The method may also include proximally retracting the tubular body following the inflation step to seat the balloon against the vessel wall.

Other aspects and features of the present invention will become apparent from consideration of the following description taken in conjunction with the accompanying drawings.

BRIEF DESCRIPTION OF THE DRAWINGS

FIG. 5A is a side view showing a stop disposed between the cartridge and occlusion member of the embodiment of FIG. 1.

FIG. 5B is a cross-sectional view of the stop of FIG. 5A, taken along line 5B-5B.

DETAILED DESCRIPTION OF THE PREFERRED EMBODIMENT

Figure 1:
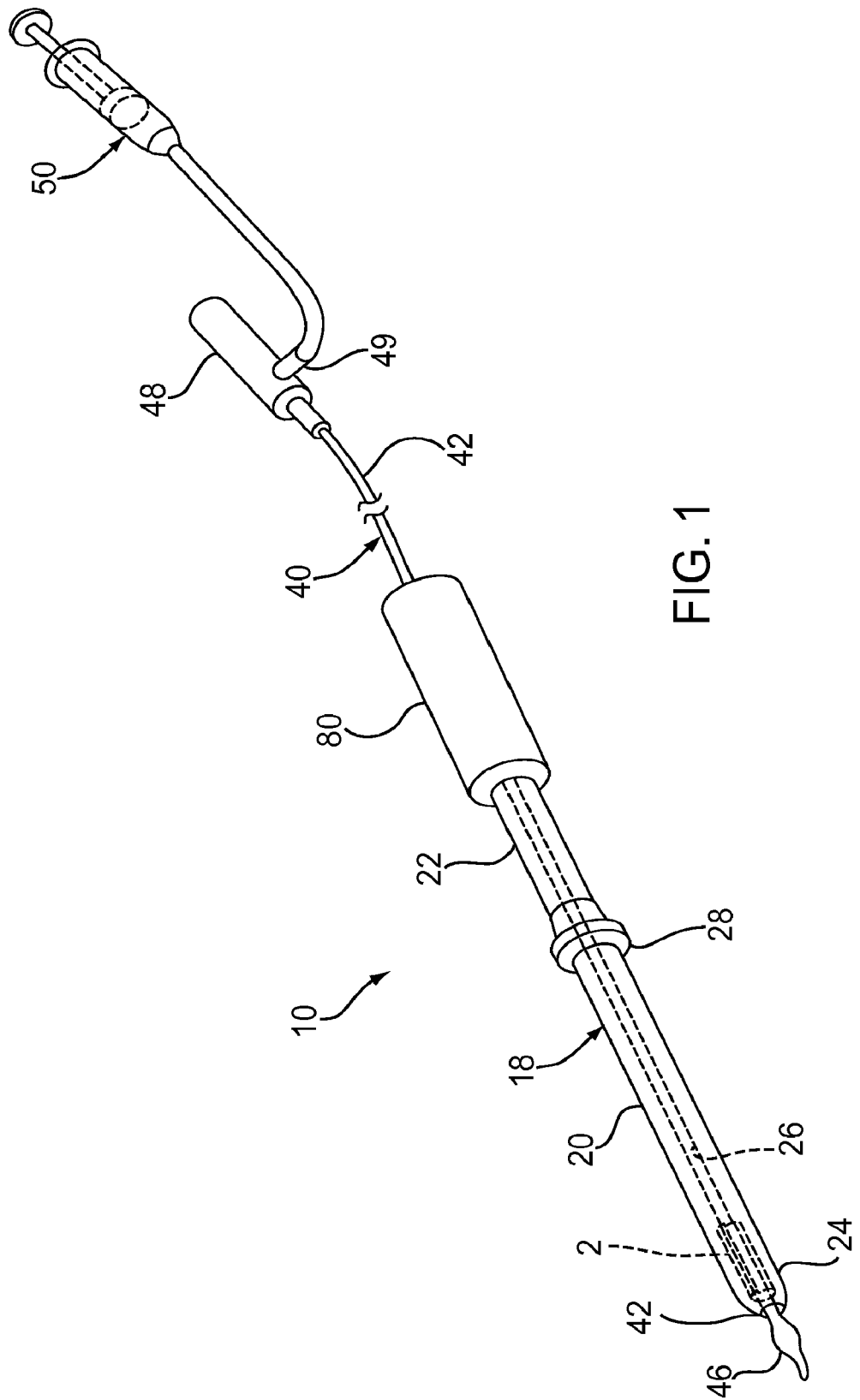
FIG. 1 is a perspective view of a first exemplary embodiment of an apparatus for delivering sealant into a puncture through tissue, including an occlusion member and a cartridge carrying the sealant.
Figure 2A:
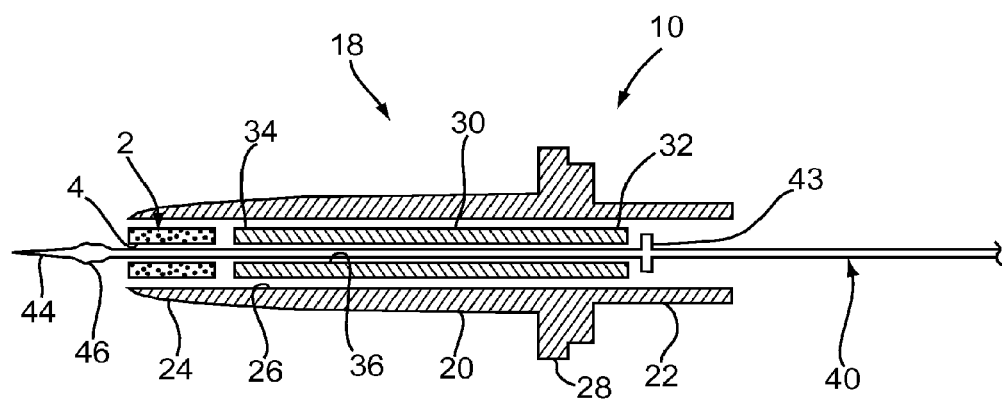
FIGS. 2A and 2B are cross-sectional views of the apparatus of FIG. 1, showing an outer member of the cartridge covering the sealant and retracted to expose the sealant, respectively.
Figure 2B:
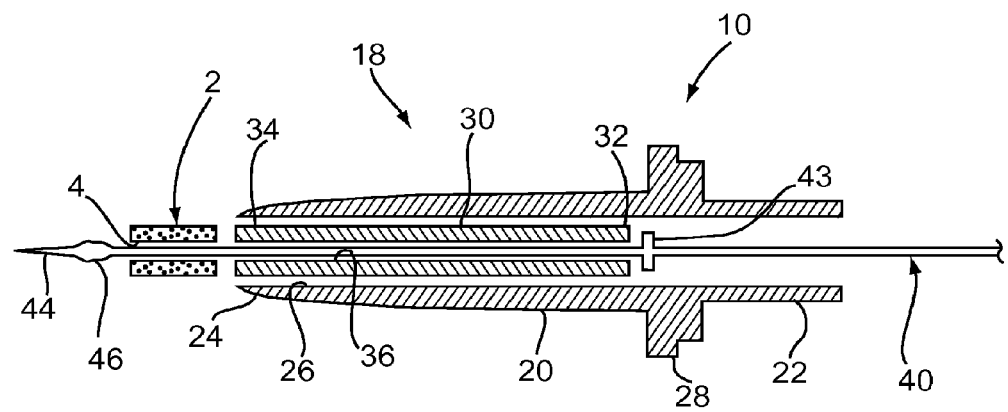

Turning to the drawings, FIGS. 1-2B shows a first exemplary embodiment of an apparatus 10 that generally includes an elongate occlusion member 40, a cartridge 18 carried by the occlusion member 40, and a sealant carried by the cartridge 18. Generally, the cartridge 18 may include an outer tubular member 20, and an inner pusher member 30 (see FIGS. 2A-2B). Optionally, as described further elsewhere herein, the cartridge 18 may include a housing or handle 80, an inner tubular member (not shown), e.g., disposed between the outer tubular member 20 and the pusher member 32, and/or a transition cuff (also not shown) between the occlusion member 40 and the cartridge 18, as described in the various embodiments herein.

The outer tubular member 20 may be a substantially rigid, semi-rigid, and/or flexible tubular body, including a proximal end 22, a distal end 24 sized and/or shaped for insertion into a puncture, and a lumen 26, e.g., extending between the proximal and distal ends 22, 24. The lumen 26 may be sized for receiving the sealant 2 and/or the pusher member 30 therein, e.g., such that the outer tubular member 18 is slidable relative to the sealant 2 and/or pusher member 30 during use, as described elsewhere herein. The distal end 24 may be tapered and/or may include a substantially atraumatic tip to facilitate advancement through a puncture.

The pusher member 30 may be an elongate tubular member, e.g., a plunger, catheter, tamping tube, and the like, including a proximal end 32, and a distal end 34 having a size for slidable insertion into the lumen 26 of the outer tubular member 20. The distal end 34 of the pusher member 30 may be substantially blunt, e.g., to facilitate contacting, pushing, compressing, and/or otherwise tamping the sealant 2, e.g., upon exposure and/or delivery into a puncture, as described elsewhere herein. The pusher member 30 may be substantially rigid, semi-rigid, and/or substantially flexible, having sufficient column strength to allow movement of the outer member 20 relative to the pusher member 30 and sealant 2 without buckling the pusher member 30. The pusher member 30 may also include a lumen 36 extending between the proximal end 32 and the distal end 34, e.g., to accommodate the elongate occlusion member 40 and/or a guidewire (not shown).

The sealant 2 may be carried by the cartridge 18, e.g., within the lumen 26 of the outer tubular member 20 adjacent to the distal end 24. Generally, the sealant 2 may have a cylindrical shape, e.g., including a lumen 4 extending between ends of the sealant, as shown. Alternatively, the sealant 2 may have other cross-sections or shapes, such as elliptical, triangular, square, conical, disk, polygonic shapes, and the like.

The sealant 2 may be formed from a biocompatible and/or bioabsorbable material, for example, a porous, bioabsorbable foam or other solid material. In one embodiment, the sealant 2 may be formed from a biocompatible and/or bioabsorbable hydrogel, e.g., polyethylene glycol ("PEG"), or other synthetic material. Exemplary hydrogel materials and methods for making them are disclosed in co-pending application Ser. No. 11/465,791, filed Aug. 18, 2006, the entire disclosure of which is expressly incorporated by reference herein.

In addition or alternatively, the sealant 2 may include pro-thrombotic material, e.g., including one or more biological pro-thrombotics, such as collagen, fibrin, carboxymethylcellulose, oxidized cellulose, alginates, gelatin, or other protein-based material, and/or synthetic materials, such as polyglycolic acids (PGA's), polyactides (PLA's), polyvinyl alcohol, and the like. The material of the sealant 2 may be at least partially absorbed by the body over time, e.g., over a period of days, weeks, or months. Optionally, the sealant 2 may include therapeutic and/or pharmaceutical agents, e.g., to promote healing, prevent infection and/or other adverse medical events, and the like. Such agents may be embedded in the sealant material and/or applied as one or more coatings or layers. In addition, the material of the sealant 2 may have a substantially uniform composition or the composition may be varied, e.g., along its length and/or within underlying layers within the sealant 2.

Optionally, the sealant 2 may include first and/or second hydrogel precursors (not shown), which may remain in an unreactive state, e.g., before or until exposure to an aqueous physiological environment. An aqueous physiological environment may exist, for example, inside a puncture track extending through tissue. For example, blood or other bodily fluids that contact the precursor-laden sealant 2 may initiate a hydrogel forming reaction between the two precursors. The reaction of the hydrogel precursors may form a cross-linked adhesive or tacky coating that may aid in retaining the sealant 2 within a puncture after deployment and/or in facilitating hemostasis within the puncture.

Optionally, an activating agent, e.g., a pH adjusting material (not shown), may also be disposed on the sealant 2 to initiate, accelerate, or otherwise enhance the reaction of the precursors. For example, the pH activating agent may create a localized change in pH after exposure to a hydrous or aqueous environment, e.g., to initiate or accelerate the hydrogel-forming reaction.

The hydrogel precursor(s) may include any number of hydrogel precursor materials, such as those disclosed in U.S. Pat. Nos. 6,152,943, 6,165,201, 6,179,862, 6,514,534, 6,379,373, 6,703,047, and in co-pending application Ser. Nos. 10/010,715 filed Nov. 9, 2001, Ser. No. 10/068,807 filed Feb. 5, 2002, and Ser. No. 10/454,362, filed Jun. 4, 2003. The disclosures of these references and any others cited therein are expressly incorporated by reference herein. Additional information regarding providing a sealant, e.g., including a core member and/or hydrogel precursors, may be found in co-pending application Ser. Nos. 10/982,387 and 10/982,384, both filed Nov. 5, 2004, the entire disclosures of which are expressly incorporated by reference herein.

With continued reference to FIG. 1, the occlusion member 40 may include a solid or hollow elongate body, including a proximal end 42, a distal end 44, and an expandable member 46 on the distal end 44. The expandable member 46 may be an inflatable and/or mechanically expandable element, such as a balloon, as shown, a wire mesh structure (not shown), an expandable frame (also not shown), and the like, as described in the applications incorporated by reference elsewhere herein. Optionally, the expandable member 46 may include a skin or other covering (not shown) on at least a proximal portion thereof, thereby making the expandable member 46 substantially nonporous. In addition or alternatively, at least a portion of the expandable member 46, may include a lubricious coating, e.g., a proximal portion and/or a covering extending at least partially over the expandable member 46.

The expandable member 46 may be selectively expandable, e.g., using one or more of a source of inflation media, e.g., a syringe 50 coupled to a lumen (not shown) extending through the elongate occlusion member 40 to an interior of the expandable member 46, a pull wire (not shown), or other actuator (also not shown) operable from the proximal end 42 of the elongate occlusion member 40. For example, as shown in FIG. 1, the occlusion member 40 may include a housing 48 on the proximal end 42 including a port 49 communicating with the syringe 50. The housing 48 may communicate with an interior of the expandable member 46 via an inflation lumen (not shown) extending between the proximal and distal ends 42, 44.

Alternatively, the expandable member 46 may be biased to the enlarged condition, but may be compressed to the contracted condition, e.g., by an overlying sleeve or other constraint (not shown). The constraint may be removed to expose the expandable member 46, allowing the expandable member 46 to automatically expand to the enlarged condition. Additional information on expandable structures that may be incorporated into elongate occlusion member 40 may be found in U.S. Pat. Nos. 6,238,412 and 6,635,068, in co-pending application Ser. Nos. 10/454,362, filed Jun. 4, 2003, 10/806,952, filed Mar. 22, 2004, 10/143,514, published as Publication No. US 2003/0078616 A1, and 11/112,877, filed Apr. 22, 2005, and 11/112,971, filed Apr. 22, 2005. The entire disclosures of these references are expressly incorporated herein by reference.

The outer tubular member 20 may be movable relative to the occlusion member 40, e.g., from a distal or first position where the distal end 24 of the outer tubular member 20 is disposed adjacent the expandable member 46 and covers the sealant 2 (FIG. 2) to a proximal or second position where the distal end 24 is retracted sufficiently to expose the sealant 2.

Optionally, as shown in FIGS. 5A and 5B, a removable spacer or other stop 70 may be provided that may extend along the occlusion member 40, e.g., between the housing 80 on the cartridge 18 and the housing 48 on the occlusion member 40. For example, the stop 70 may be an elongate member 72 having a "C" shaped cross-section, allowing the stop 70 to be snapped or otherwise received around the occlusion member 40. The stop 70 may have sufficient length such that a first end 76 thereof abuts the proximal end 22 of the outer tubular member 20 and/or the housing 80 in the first position and a second end 74 thereof abuts the housing 48 on the proximal end 42 of the occlusion member 40. Thus, with the stop 70 received around the occlusion member 40, proximal movement of the outer tubular member 40 from the first position shown in FIG. 2A is prevented. The stop 70 may be peeled or otherwise separated from around the occlusion member 40, e.g., by pulling tab 78 or other handle (not shown), thereby allowing the outer tubular member 20 to be subsequently directed proximally.

Returning to FIG. 2B, with the stop removed, the outer tubular member 20 may be directed proximally to the second position to expose the sealant 2. To facilitate retraction of the outer tubular member 20, a raised slider ring, handle, or other radial element 28 may be provided on the outer tubular member 20 between the proximal and distal ends 22, 24. The slider ring 28 may be attached to an outer surface of the outer tubular member 20. Alternatively, the slider ring 28 may be integrally formed with the outer tubular member 20 or may be a separate proximal extension attached to the outer tubular member 20, e.g., at least partially defining the proximal end 22 of the outer tubular member 20.

Turning to FIGS. 3A-3D, an exemplary method is shown for sealing a puncture 90 using the apparatus 10. Generally, the puncture 90 may extend from a patient's skin 92 through intervening tissue 96, e.g., to a body lumen 94. In an exemplary embodiment, the puncture 90 may be a percutaneous puncture communicating with a blood vessel 94, such as a femoral artery, carotid artery, and the like.

In an exemplary method, the puncture 90 may be created using known procedures, e.g., using a needle, guidewire, one or more dilators, and the like (not shown). An introducer sheath 98 may be advanced through the puncture 90 into the vessel 94, e.g., to provide access into the vessel 90 for one or more instruments, and/or allow one or more diagnostic and/or interventional procedures to be performed via the vessel 90. Upon completing the procedure(s) via the vessel 94, any instruments and/or the introducer sheath 98 may be removed from the puncture 90.

Figure 3A:
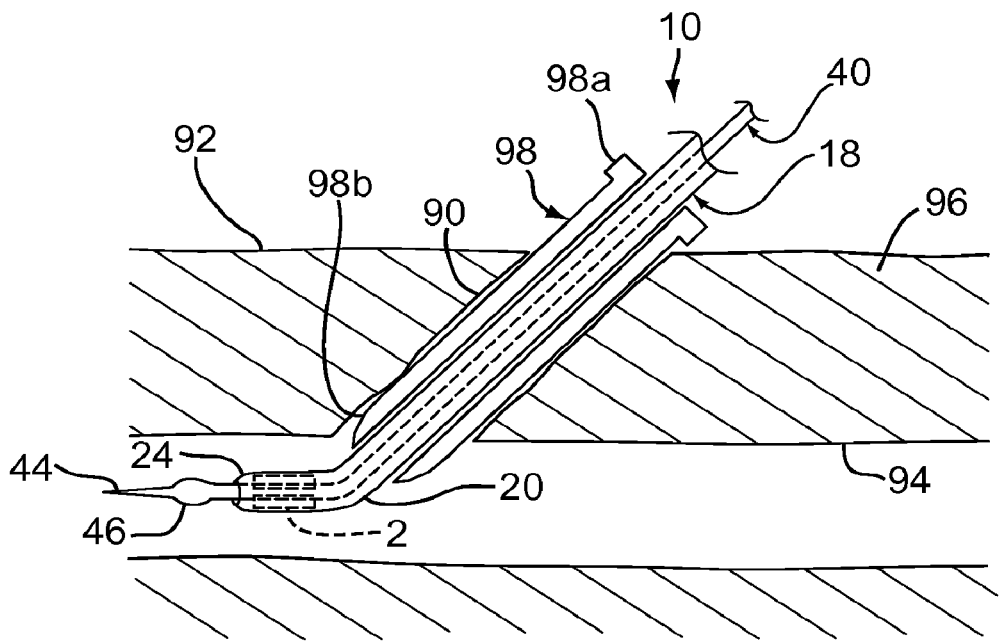
FIGS. 3A-3D are cross-sectional views of a patient's body, showing a method for sealing a puncture extending through tissue to a body lumen using the apparatus of FIG. 1.

Turning to FIG. 3A, with the expandable member 46 collapsed, the apparatus 10 may be introduced into the puncture 90, e.g., by inserting the distal end 44 of the occlusion member 40 into the introducer sheath 98 (if the introducer sheath has not already been removed from the puncture 90 after using the introducer sheath 98 to access the vessel 94). As the distal end 44 of the occlusion member 40 is advanced through the introducer sheath 98 and puncture 90, the cartridge 18, e.g., the distal end 24 of the outer tubular member 20, follows the expandable member 46 through the puncture 90 and into the vessel 94. Thus, the sealant 2 within the cartridge 18 may be advanced through the puncture 90 and into the vessel 94, while remaining within the outer tubular member 20.

The occlusion member 40 and cartridge 20 may be sufficiently long such that, when the slider ring 28 (not shown in FIG. 3A) contacts a proximal end 98a of the introducer sheath 98, the occlusion member 40 extends distally beyond a distal end 98b of the introducer sheath 98. In addition or alternatively, the occlusion member 40 may include distance markers, bands, numbers, and the like (not shown), to indicate to the user the depth to which the occlusion member 40 has been inserted, which may facilitate confirming that the apparatus 10 has been advanced sufficiently to dispose the expandable member 46 within the vessel 94 beyond the distal end 98b of the introducer sheath 98.

Figure 3B:
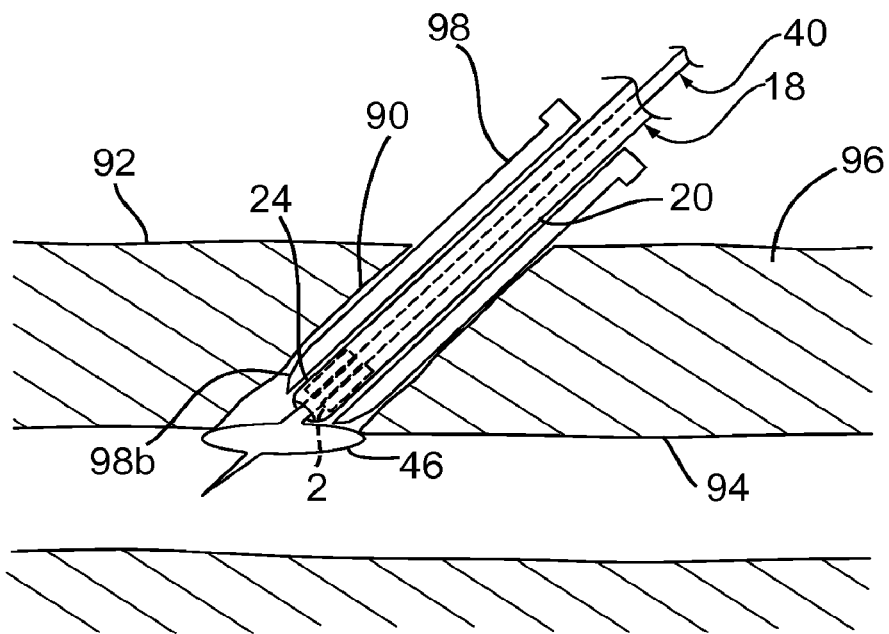

Turning to FIG. 3B, once the expandable member 46 is disposed within the vessel 94 beyond the introducer sheath 98, the expandable member 46 may be expanded, e.g., by delivering inflation media into the expandable member 46. With the expandable member 46 expanded, the apparatus 10 may be withdrawn until the expanded expandable member 46 contacts a wall of the vessel 94 immediately adjacent the puncture 90.

For example, the apparatus 10 may be retracted until the expandable member 46 contacts the distal end 98b of the introducer sheath 98. Further withdrawal of the apparatus 10 may cause the expandable member 46 to push the introducer sheath 98 at least partially out of the puncture 90 until the expandable member contacts the wall of vessel 94 immediately adjacent the puncture 90, similar to methods described in application Ser. No. 10/982,384, incorporated by reference elsewhere herein. Proximal tension may be maintained on the occlusion member 40 to substantially seal the puncture 90 from the vessel 94 using the expandable member 46 or simply to maintain the expandable member 46 in contact with the wall of the vessel 90 and/or to maintain the occlusion member 40 under tension.

Figure 3C:
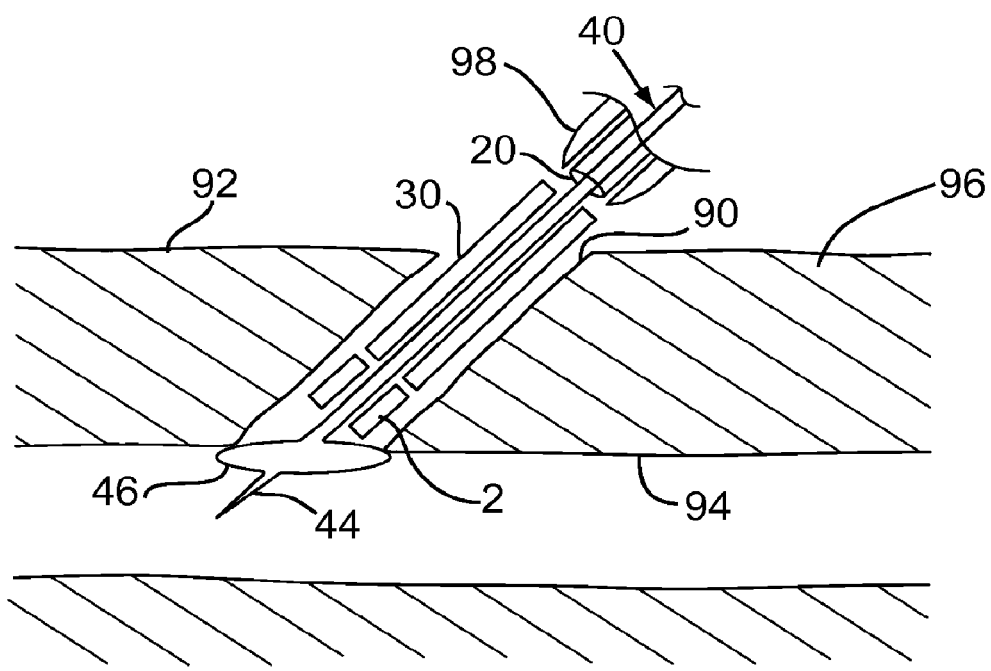

Turning to FIG. 3C, the outer tubular member 20 may then be retracted to expose the sealant 2 within the puncture 90. For example, the introducer sheath 98 may be withdrawn from the puncture 90, thereby causing the introducer sheath 98 to contact the slider ring 28 and pull the outer tubular member 20 proximally out of the puncture 90. Alternatively, the outer tubular member 20 may be withdrawn before withdrawing the introducer sheath 98 or the introducer sheath 98 may have been withdrawn before introducing the apparatus 10. As shown, the inner pusher member may be at least partially exposed as the outer tubular member 20 (and introducer sheath 98) are withdrawn from the puncture 90.

With additional reference to FIGS. 2A and 2B, the occlusion member 40 may include a stop 43 that prevents proximal movement of the pusher member 30 while the outer tubular member 20 is retracted. Otherwise, the pusher member 30 may be free to slide distally relative to the occlusion member 40 (but for the sealant 2). Thus, the pusher member 30 may remain substantially stationary while the outer tubular member 20 is retracted. Consequently, the sealant 2 may abut the distal end 34 of the pusher member 30 to prevent the sealant 2 from also moving proximally while the outer tubular member 20 is retracted.

If desired, the pusher member 30 may be used to compress, pack, or otherwise tamp the sealant 2 within the puncture 90. For example, after the sealant 2 is exposed within the puncture 90, the pusher member 30 may be advanced manually to tamp the sealant 2 distally against the expandable member 46. This may place the distal end 16 of the sealant 2 adjacent to or against the wall of the vessel 94 and/or deform the sealant 2, which may enhance hemostasis in the arteriotomy between the vessel 94 and the puncture 90.

Optionally, after the sealant 2 is deployed within the puncture 90, additional sealing compound may be delivered into the puncture 90, e.g., to fill all or a portion of the puncture 90 above and/or around the sealant 2. For example, the lumen 36 of the inner pusher member 30 may be used to deliver liquid sealing compound, e.g., hydrogel precursors (not shown), into the puncture 90. Exemplary apparatus and methods for delivering such sealing compounds into the puncture 90 are disclosed in co-pending application Ser. Nos. 10/454,362 and 10/806,952, filed Mar. 22, 2004, the entire disclosures of which are expressly incorporated by reference herein.

Figure 3D:
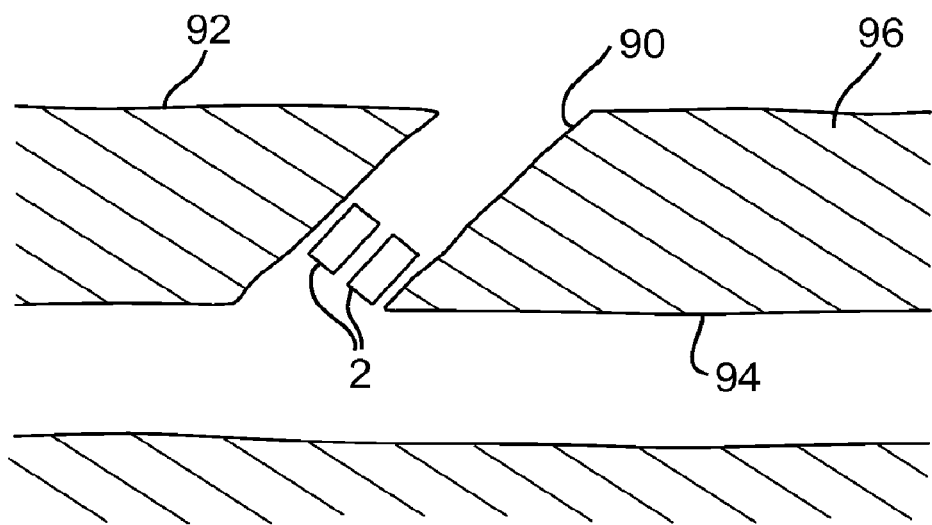

Turning to FIG. 3D, the occlusion member 40 may be withdrawn through the sealant 2 and the lumen 36 of the inner pusher member 30. The inner pusher member 30 may restrain the sealant 2 from moving proximally as the elongate occlusion member 40 is removed. Thus, the occlusion member 40, which may still carry the outer tubular member 20 and/or introducer sheath 98, may be completely removed, leaving the pusher member 30 and sealant 2 within the puncture. Once the elongate occlusion member 40 is removed, the pusher member 30 may be removed, leaving the sealant 2 to seal the puncture 90.

When the expandable member 46 is collapsed, blood and/or other fluid within the vessel 94 may enter the puncture 90, thereby exposing the sealant 2 to an aqueous physiological environment. The aqueous physiological environment, which may include blood or other bodily fluids from the vessel 94 (or other body lumen) may wet the sealant 2, thereby hydrating the sealant material and/or initiating a reaction between precursor components carried by the sealant 2, as described in the applications incorporated by reference above.

Figure 4A:
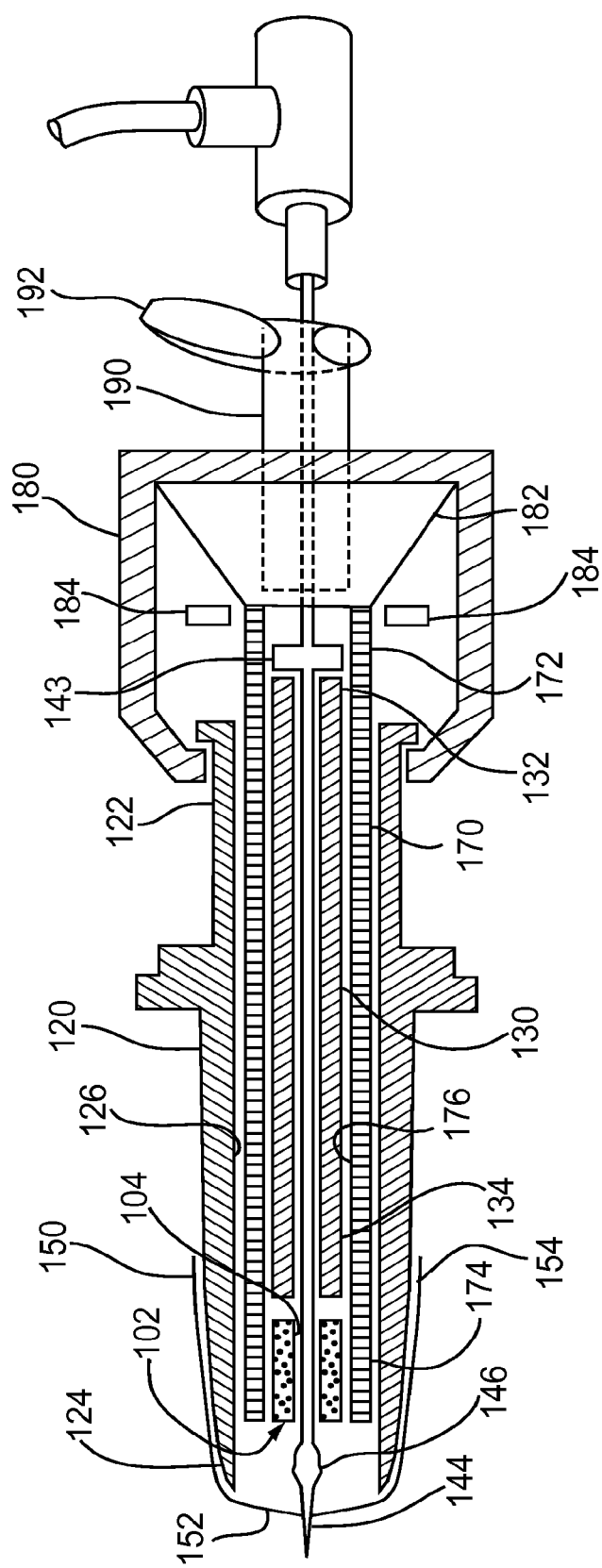
FIGS. 4A-4C are cross-sectional views of a second embodiment of an apparatus for delivering a sealant into a puncture through tissue, showing the apparatus manipulated between first, second, and third positions, respectively.
Figure 4B:
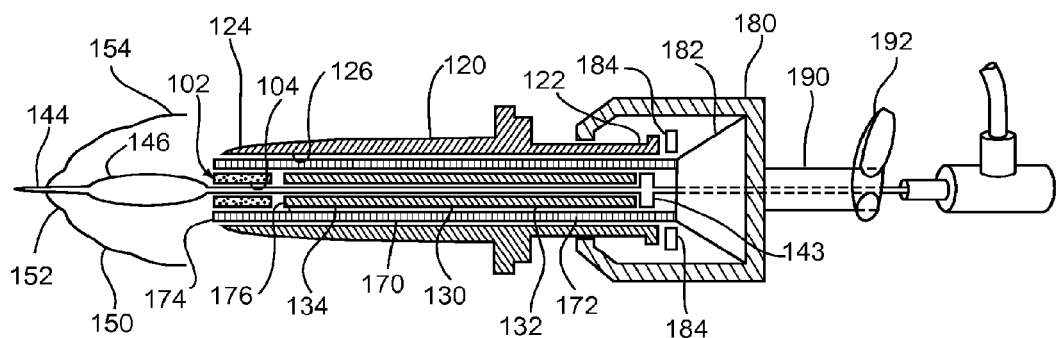
Figure 4C:
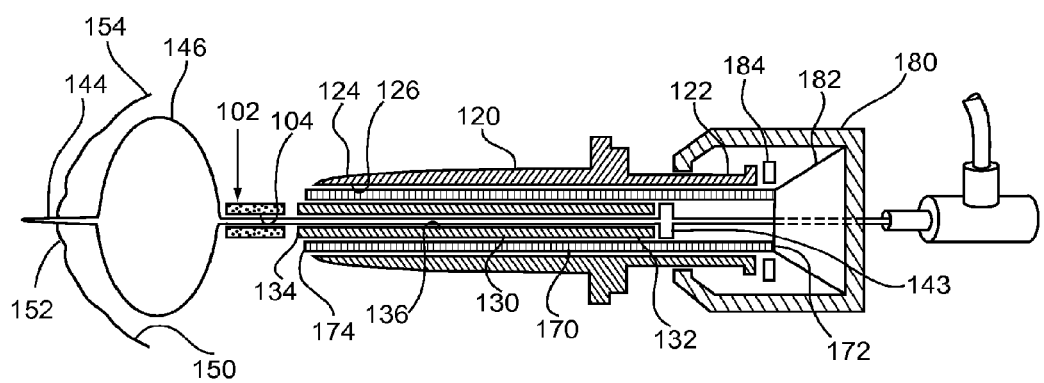

Turning now to FIGS. 4A-4C, another exemplary embodiment of an apparatus 110 is shown that generally includes an occlusion member 140, a cartridge 118, and a sealant 102, similar to the previous embodiments. The occlusion member 140 includes an elongate member having a proximal end 142, a distal end 144, and an expandable member 146 on the distal end 144, also similar to previous embodiments.

The cartridge 118 generally includes an outer tubular member 120, and an inner pusher member 130, also similar to the previous embodiments. The outer tubular member 120 may be a tubular member including a proximal end 122, a distal end 124 sized and/or shaped for introduction into a puncture (not shown), and a lumen 126 extending therebetween.

Unlike the previous embodiments, the cartridge 118 also includes an inner tubular member 170 disposed between the outer tubular member 120 and the pusher member 130, and a housing 180 on the proximal end 122 of the outer tubular member 120, e.g., coupled to at least one of the outer tubular member 120 and the inner tubular member 170. As shown, the inner tubular member 170 includes a proximal end 172 coupled to an inner hub 182 within the housing 180, a distal end 174 disposed over the sealant 102, and a lumen 176 extending between the proximal and distal ends 172, 174, e.g., for slidably receiving the sealant 102 and pusher member 130. Initially, the distal end 174 of the inner tubular member 170 may be disposed proximal to the distal end 124 of the outer tubular member 120, as described further below.

The inner tubular member 170 may be substantially stationary relative to the housing 180, e.g., by fixing the inner hub 182 within or otherwise relative to the housing 180. For example, the inner hub 182 may be shaped to sit within a correspondingly shaped cavity within the housing 180. In addition or alternatively, the inner hub 182 may be secured to the housing 180, e.g., using adhesives, connectors, sonic welding, fusing, and the like.

The outer tubular member 120 may be slidable axially relative to the housing 180, inner tubular member 170, and/or the occlusion member 140. For example, the outer tubular member 120 may be slidable proximally relative to the housing 180 (and inner tubular member 170 if fixed relative to the housing 180) between a distal or first position, shown in FIG. 4A, and a proximal or second position, shown in FIG. 4B. As shown in FIG. 4A, the outer tubular member 120 is shown in the first position, e.g., in which the apparatus 110 may be initially provided to a user. In the first position, the distal end 124 of the outer tubular member 120 may overly the expandable member 46, i.e., distally beyond the distal end 174 of the inner tubular member 170 and the sealant 2 disposed within the inner tubular member 170. Thus, the distal end 124 of the outer tubular member 120 may cover all of the other components of the apparatus 110 to facilitate introduction into a puncture.

Optionally, as shown in FIGS. 4A and 4B, a transition cuff or sleeve 150 may be provided that includes a first end 152 attached to the distal end 144 of the occlusion member 140 distally beyond the expandable member 146 and a second loose end 154. The transition cuff 150 may be formed from a substantially thin-walled and/or flexible material, e.g., similar to the expandable element 146. The transition cuff 150 may provide a substantially atraumatic tip for the apparatus 110. As shown in FIG. 4A, initially, the distal end 144 of the occlusion member 140 may extend distally beyond the distal end 124 of the outer tubular member 120, and the transition cuff 150 may extend from the distal end 144 of the occlusion member 140 such that the second end 154 extends over the distal end 124 of the outer tubular member 120.

As shown in FIG. 4B, when the outer tubular member 120 is retracted to the second position, the second end 154 of the transition cuff 150 may be separated from the distal end 124 of the outer tubular member 120. The transition cuff 150 may extend loosely over the expandable member 146 or may resiliently retract to expose the expandable member 146. When the expandable element 146 is subsequently expanded, the second end 154 of the transition cuff 150 may slide off the distal end of the expandable element 146 and/or the transition cuff 150 may otherwise fold or collapse adjacent to the expandable element 146.

If desired, a lubricious coating may be applied to the transition cuff 150 and/or the expandable member 146, e.g., to ease the transition cuff 150 sliding or otherwise retracting from over the expandable member during the expansion of the expandable element 146. Alternatively, the material of the transition cuff 150 may be sufficiently resilient to expand when the expandable member 146 is expanded, instead of sliding off the expandable member 146.

With additional reference to FIGS. 4B and 4C, the housing 180, including the inner and outer tubular members 170, 120 may be movable together from the second position, shown in FIG. 4B, to a third position, shown in FIG. 4C, wherein the distal ends 174, 124 of the inner and outer tubular members 170, 120 are retracted sufficiently to expose the sealant 102.

Optionally, the proximal end 122 of the outer tubular member 120 may include one or more features, e.g., an annular protrusion 123, that limits distal movement of the outer tubular member 120. For example, the annular protrusion 123 may abut a distal end of the housing 180 in the first position, thereby preventing further distal movement of the outer tubular member 120, but allowing proximal motion from the first position towards the second position.

Optionally, the outer tubular member 120 and/or housing 180 may include a safety mechanism to prevent premature proximal movement of the outer tubular member 120 from the first position. For example, an actuator (not shown) may be provided on the housing 180 that includes a detent, catch, or other feature (also not shown) that engages a pocket, mating detent, catch, or other feature (also not shown) on the proximal end 122 of the outer tubular member 120. With the features engaged, the outer tubular member 120 may be restrained from proximal movement. During use, the actuator, e.g., a button, slider, latch, and the like, on the housing 180 may then be actuated to release the features, thereby allowing the outer tubular member 120 to be directed proximally from the first position.

In addition or alternatively, similar actuators or releases may be provided between the housing 180 and the occlusion member 140 for selectively preventing movement of the housing 180 relative to the occlusion member 140.

In another alternative, a removable spacer or other stop 190 may be provided that may extend from the proximal end of the housing 180 to the proximal end 142 of the occlusion member 140. For example, the stop 190 may be an elongate member having a "C" shaped cross-section, allowing the stop 190 to be snapped or otherwise received around the occlusion member 140. Alternatively, the stop 190 may be a tubular member received around the occlusion member 140 that includes one or more weakened regions, e.g., axial seams, that allow the stop 190 to separated and removed from around the occlusion member 140.

The stop 190 may have sufficient length to abut the proximal end of the housing 180 and the housing 148 on the proximal end 142 of the occlusion member 140. The stop 190 may also have sufficient column strength to prevent the housing 180 from being directed proximally and causing the stop 190 to buckle or otherwise fail. Thus, with the stop 190 received around the occlusion member 140, proximal movement of the housing 180 may be substantially prevented. The stop 190 may be peeled or otherwise separated from around the occlusion member 40, e.g., by pulling tab or handle 192, thereby allowing the housing 180 to be subsequently directed proximally. As shown in FIG. 4C, the housing 180, along with the inner and outer tubular members 170, 120 may then be directed proximally to the third position to expose the sealant 102.

To facilitate retraction of the outer tubular member 120 from the first position to the second position, a raised slider ring or other radial element 128 may be provided on the outer tubular member 120 between the proximal and distal ends 122, 124. The slider ring 128 may be attached to an outer surface of the outer tubular member 120. Alternatively, the slider ring 128 may be integrally formed with the outer tubular member 120 or may be a separate proximal extension attached to the outer tubular member 120, e.g., at least partially defining the proximal end 122 of the outer tubular member 120.

Optionally, the housing 180 may include one or more stops 184 for limiting proximal movement of the outer tubular member 120 relative to the housing 180. For example, as best seen in FIG. 4B, the stop(s) 184 may be one or more tabs or walls extending at least partially across the housing 180 such that the proximal end 122 of the outer tubular member 20 abuts the stop(s) 184 when the outer tubular member 120 has been retracted to the second position, thereby preventing further retraction of the outer tubular member 120, which may expose the inner tubular member 170 and/or sealant 102 prematurely.

In addition or alternatively, the slider ring 128 may be located a predetermined distance from the proximal end 122 of the outer tubular member 120 (and consequently the distal end of the housing 180) such that the slider ring 128 abuts the housing 180 when the outer tubular member 120 is retracted to the second position, thereby preventing further proximal movement of the outer tubular member 120.

Optionally, the outer tubular member 120 and/or housing 180 may include one or more detents, stops, pockets, or other features (not shown) that secure the outer tubular member 120 relative to the housing 180 when the outer tubular member 120 has been retracted to the second position. For example, the slider ring 128 may include an annular ridge (not shown) that may be received into a corresponding shaped recess (also not shown) in the distal end of the housing 180. The ridge and recess may be shaped to allow the ride to be forced into the recess, but not subsequently removed. Alternatively, one or more detents or other interlocking connectors may be provided on the proximal end 122 of the outer tubular member 120 and the housing 180 or inner tubular member 170 that engage one another once the outer tubular member 120 has been directed to the second position. Thus, these feature(s) may prevent the outer tubular member 120 from being advanced distally from the second position, e.g., to cover again the exposed sealant 102, and/or may synchronize subsequent movement of the outer tubular member 120 to movement of the housing 180 and/or inner tubular member 170.

Similar to the previous embodiments, the pusher member 130 may include a proximal end 132, a distal end 134, and a lumen 136 extending therebetween. The pusher member 130 may be slidable over the occlusion member 140, although the occlusion member 140 may include one or more stops 143 to limit proximal movement of the pusher member 130, while allowing distal movement.

Similar to the method described above with respect to the FIGS. 3A-3D, the apparatus 110 may be used to deliver the sealant 102 within a puncture through tissue, e.g., communicating with a blood vessel or other body lumen (not shown). Initially, an introducer sheath may be placed within the puncture 90, e.g., to provide access to vessel 94, similar to previous embodiments.

After completing any procedures performed via the introducer sheath, the apparatus 110 is introduced into the puncture through the introducer sheath with the outer tubular member 120 in the first position shown in FIG. 4A. During this introduction, the transition cuff 150, if provided, may extend over the distal end 124 of the outer tubular member 120, e.g., to provide a smooth transition, seal the lumen 126 of the outer tubular member 120, and/or otherwise facilitate introduction. In particular, the distal end 124 of the outer tubular member 120 may be introduced into the introducer sheath, and advanced until the distal end 124 is exposed within the vessel.

With the distal end 124 exposed within the vessel, the outer tubular member 120 may be retracted to the second position shown in FIG. 4B. As the outer tubular member 120 is retracted, the second end 154 of the transition cuff 150 is removed from over the distal end 124, and the transition cuff 150 may resiliently retract at least partially from over the expandable member 146. As shown in FIG. 4B, the expandable member 146 of the occlusion member 140 is fully exposed when the outer tubular member 120 is retracted to the second position.

In an alternative embodiment, the apparatus 110 may be advanced until the slider ring 128 abuts the proximal end of the introducer sheath. As the apparatus 110 is advanced further, the slider ring 128 may prevent further advancement of the outer tubular member 120, while the other components of the apparatus 110 continue to be advanced. Thus, in essence, the outer tubular member 120 is retracted by advancing the other components of the apparatus 110, rather than pulling the outer tubular member 120. This alternative may be advantageous, because it may reduce a manipulating step by the user.

With the expandable member 146 of the occlusion member 140 exposed within the vessel, the expandable member 146 is expanded. As the expandable member 146 is expanded, the transition cuff 150 may slide off the expandable member 146, fold or otherwise, retract, and/or expand with the expandable member 146.

The occlusion member 140 may then be at least partially withdrawn until the expanded expandable member 146 contacts the wall of the vessel, e.g., to substantially seal the vessel from the puncture. This may involve a two-step, tactile process, as described elsewhere herein, in which the expanded expandable member 146 is withdrawn until it contacts the distal end 164 of the introducer sheath and then until the expandable member 146 contacts the wall of the vessel (thereby pulling the introducer sheath partially out of the puncture). Tension in the proximal direction may be applied and/or maintained on the occlusion member 140 to hold the expandable member 146 against the wall of the vessel and/or seal the puncture.

Turning to FIG. 4C, the housing 180 and inner and outer tubular members 170, 120 may then be retracted to the third position to expose the sealant 102 within the puncture. This may be achieved by pulling the slider ring 128 on the outer tubular member 120, thereby pulling the outer tubular member 120 and housing 180 proximally out of the puncture. Alternatively, the introducer sheath may be pulled proximally, thereby causing the introducer sheath to abut the slider ring 128, and then the housing 180 to withdraw the components of the apparatus 110 at least partially out of the puncture.

Similar to the previous embodiments, since occlusion member 140 includes stops 143 to prevent proximal movement of the pusher member 130 relative to the occlusion member 140, the pusher member 130 may remain substantially stationary while the inner and outer tubular members 170, 120 are retracted to expose the sealant 102 and the pusher member 130. Thus, the pusher member 130 may serve as a stop that prevents the sealant 102 from moving proximally while the inner tubular member 170 around the sealant 102 is withdrawn.

In one embodiment, the user of the apparatus 110 may position his or her thumb on the pusher member 130 to maintain its position while the other components of the cartridge 118 are retracted and/or removed entirely from the puncture.

Optionally, the sealant 102 may then be tamped within the puncture, e.g., by advancing the pusher member 130 distally to press the sealant 102 against the wall of the vessel and/or against the expandable member 146, similar to the previous embodiments.

After delivering the sealant 102, the proximal tension on the occlusion member 140 may be released, the expandable member 146 may be collapsed, and the occlusion member 140 may be slowly withdrawn through the lumen of the sealant 102. This may be achieved simply by pulling on the introducer sheath until the housing 180 contacts the housing 148 of the occlusion member 140, and continuing to pull to pull the occlusion member 140 out of the puncture.

After removing the occlusion member 140, the pusher member 130 may be withdrawn, leaving the sealant 102 in place.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. A method of sealing a puncture through a vessel wall, comprising the steps of:
    positioning a sealing device through a vascular puncture such that an inflatable balloon carried by an elongate, tubular body and an outer tubular member extend into the vessel, and a sealant is carried by the elongate tubular body adjacent the balloon prior to positioning the sealing device through the vascular puncture;
    inflating the balloon inside of the vessel;
    retracting the outer tubular member to expose the sealant;
    deflating the balloon; and
    retracting the balloon through the sealant, leaving the sealant in place.

2. A method of sealing a puncture through a vessel wall as in claim 1, further comprising the step of tamping the sealant.

3. A method of sealing a puncture through a vessel wall as in claim 2, wherein the tamping step is accomplished using an elongate tamping tube, slidably carried inside of the outer tubular member.

4. A method of sealing a puncture through a vessel wall as in claim 1, further comprising the step of proximally retracting the tubular body following the inflation step to seat the balloon against the vessel wall.

5. A method of sealing a puncture through a vessel wall as in claim 3, further comprising the step of proximally retracting the balloon through the tamping tube.

* * * * *